(12) United States Patent  
Wruck

(10) Patent No.: US 10,179,221 B2
(45) Date of Patent: Jan. 15, 2019

(54) DEVICE AND METHOD FOR PROVIDING A BREATHING GAS STREAM

(71) Applicant: Dräger Medical GmbH, Lübeck (DE)

(72) Inventor: Norbert Wruck, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 977 days.

(21) Appl. No.: 14/168,486

(22) Filed: Jan. 30, 2014

(65) Prior Publication Data

US 2014/0216446 A1 Aug. 7, 2014

(30) Foreign Application Priority Data

Feb. 2, 2013 (DE) .................. 10 2013 001 888

(51) Int. Cl.
| | | |
|---|---|---|
| *A61M 16/00* | (2006.01) | |
| *A61M 16/10* | (2006.01) | |
| *A61M 16/14* | (2006.01) | |
| *A61M 16/16* | (2006.01) | |
| *A61M 16/08* | (2006.01) | |
| *A61M 16/12* | (2006.01) | |

(52) U.S. Cl.
CPC .... *A61M 16/1045* (2013.01); *A61M 16/0057* (2013.01); *A61M 16/109* (2014.02); *A61M 16/1095* (2014.02); *A61M 16/142* (2014.02); *A61M 16/16* (2013.01); *A61M 16/0875* (2013.01); *A61M 16/1065* (2014.02); *A61M 16/12* (2013.01); *A61M 2205/3368* (2013.01)

(58) Field of Classification Search
CPC .......... A61M 16/0057; A61M 16/0875; A61M 16/1045; A61M 16/142; A61M 16/14; A61M 16/147; A61M 16/18; A61M 16/1095; A61M 16/16; A61M 16/109; A61M 2205/3368; A61M 16/1065; A61M 16/12

USPC .......................... 128/203.12, 203.15, 203.16
See application file for complete search history.

(56) References Cited

U.S. PATENT DOCUMENTS

| 3,871,373 | A | | 3/1975 | Jackson | |
|---|---|---|---|---|---|
| 5,388,571 | A | * | 2/1995 | Roberts | ................. A61M 16/16 |
| | | | | | 128/200.18 |

(Continued)

FOREIGN PATENT DOCUMENTS

| EP | 0 535 952 B1 | 12/1997 |
|---|---|---|
| WO | 2012/020004 A1 | 2/2012 |
| WO | 2012/025496 A1 | 3/2012 |

*Primary Examiner* — Gregory Anderson
*Assistant Examiner* — Victoria Murphy
(74) *Attorney, Agent, or Firm* — McGlew and Tuttle, P.C.

(57) ABSTRACT

A device 10 for providing a breathing gas stream, which contains a therapeutically active substance, for the mechanical respiration and/or mechanical breathing assistance of a patient, wherein the device 10 has at least one first line 21, through which a first gas stream 31 flows during the operation of the device, and wherein the device 10 has at least one second line 22, wherein the first line 21 and the second line 22 have a common section 13, and wherein the first line 21 and the second line 22 are connected to one another by a water vapor-permeable membrane 24 in the area of the common flow section 13, the present invention provides for a second gas stream 32 to flow through the second line 22 during the operation of the device.

13 Claims, 2 Drawing Sheets

(56) References Cited

U.S. PATENT DOCUMENTS

2001/0054422 A1* 12/2001 Smith ................... A61M 16/08
                                                        128/200.24
2002/0195104 A1   12/2002 Fini et al.
2007/0083677 A1*  4/2007 Cecka ................ A61M 16/208
                                                        710/1

* cited by examiner

DEVICE AND METHOD FOR PROVIDING A BREATHING GAS STREAM

CROSS REFERENCE TO RELATED APPLICATIONS

This application claims the benefit of priority under 35 U.S.C. § 119 of German Patent Application DE 10 2013 001 888.9 filed Feb. 2, 2013, the entire contents of which are incorporated herein by reference.

FIELD OF THE INVENTION

The present invention pertains to a device for providing a breathing gas stream, which contains a therapeutically active substance, for the mechanical respiration and/or mechanical breathing assistance of a patient, wherein the device has a first line through which a gas stream flows during the operation and a second line, wherein the first line and the second line have a common flow section and are connected to one another in the area of the common flow section by a water vapor-permeable membrane, as well as to a method for providing such a breathing gas stream and to the use of a corresponding device in such a method.

BACKGROUND OF THE INVENTION

Mechanical respiration and mechanical breathing assistance are usually used in respiration if the spontaneous breathing of a patient is insufficient or even not present at all. If spontaneous breathing is insufficient, mechanical breathing assistance is often sufficient. The patient must be respirated with a machine in the absence of spontaneous breathing. There are a number of different forms of respiration, in case of both mechanical respiration and mechanical breathing assistance, but they all have in common the fact that a breathing gas stream is fed to the patient to be treated in a controlled manner.

One or more therapeutically active substances may also be added to such a breathing gas stream, and these substances can be administered to the patient in this manner by inhalation. Such therapeutically active substances may be, for example, anti-infectious agents, for example, substances with antibacterial action, e.g., antibiotics; substances with antiviral action, or substances with antimycotic action. Immunomodulators or substances for the treatment of the lung surface, for example, artificial pulmonary surfactants, may also be administered.

Corresponding substances to be administered are usually transformed into a state in which they are carried by the gas from a liquid or solid, for example, powdered state by means of an atomizer, so that they can be fed as an aerosol into the breathing gas stream. An aerosol is usually defined here as a dispersion of a solid or of a liquid, especially of solid or liquid suspended particles (aerosol particles), in a gas (carrier gas). The aerosol prepared can then be fed into the breathing gas stream and flow together with the breathing gas stream into the patient's airways. For example, so-called "metered dose inhalers" (MDI) are used for atomization. The aerosol particles can reach, for example, the alveoli in the lungs, where they are taken up by the patient via the lung epithelium.

Besides the treatments of special pulmonary diseases in adults, the administration of therapeutic active substances to newborn and premature babies in this way is of great interest as well. For example, the administration of surfactant can make a decisive contribution to the treatment of the so-called Neonatal Respiratory Distress Syndrome (NRDS). Pulmonary surfactants are developed too weakly in premature and newborn babies who have this disease. This implies the risk that the alveoli of the not yet fully matured lungs collapse in themselves and stick together. The gas exchange area of the lungs can thus decrease considerably, so that respiratory distress syndrome develops. A deficiency of pulmonary surfactants may lead to respiratory distress syndrome (adult respiratory distress syndrome, ARDS) in adults as well. Respiratory distress syndrome can be treated or prevented in both cases by the administration of an artificial surfactant. This artificial surfactant to be administered is typically a phospholipid protein composition, which affects the surface tension at the interface between lung tissue and air in the alveoli.

Independently from the administration of therapeutic substances, it is usually necessary during the artificial respiration or breathing assistance of a patient to humidify the breathing gas stream administered in a physiologically adequate manner. This is important to prevent the ciliary epithelium from drying out and an increased risk for pneumonia, which is associated therewith. Moisture is therefore usually fed to the breathing gas stream in a controlled manner.

For example, EP 0 535 952 B1 provides for an air humidifier, in which a breathing gas stream is sent through a humidifying chamber having a gas inlet and a gas outlet. The humidifying chamber is arranged above a hot plate, so that the breathing gas stream leaving the humidifying chamber is humidified in a physiological manner and is brought to an adequate temperature.

U.S. Pat. No. 3,871,373 also describes a device for humidifying and administering a gas to a patient. The device has a gas line, which delivers oxygen as well as optionally an anesthetic. The gas line has a wall, which may be permeable to water vapor. The device has, furthermore, a water chamber, which extends along a common section with the gas line and through which liquid water is transported. The water chamber is likewise defined by the water vapor-permeable wall, so that the liquid water can evaporate through this wall into the gas line. The oxygen stream flowing through the gas line is humidified in this manner before it reaches the respiratory tract of the patient to be treated.

For administering an aerosol to a patient with simultaneous breathing assistance, WO 2012/020004 A1 provides for a device, which comprises a source for a breathing gas, on the one hand, and a source for an aerosol, on the other hand. A so-called aerosol flow, i.e., an aerosol stream, which is led into the device tangentially, i.e., at right angles to the breathing gas stream originating from the breathing gas source, is generated from the aerosol source in this device. This device is used especially to prevent deposits from forming in the device or in the upper airways during the administration of surfactant.

Even though it is known in all these solutions that the breathing gas itself is humidified, it is problematic that the part of the stream that carries the therapeutically active substance, i.e., the aerosol, is not humidified or is not humidified sufficiently or cannot be humidified or cannot be humidified sufficiently. In particular, the problem may frequently occur that the therapeutically active substances are present as dry solids before they can be atomized. However, the risk that the substance will form lumps may develop as soon as this dry solid substance comes into contact with moisture, so that the aerosol particles formed become much too large and cannot enter the alveoli of the lungs any longer.

The substance may already become stuck in this atomized state in this manner in the worst case. However, there is a risk in both cases that a specific and controlled metering of the therapeutically active substance cannot be ensured any more to the extent at which this is often necessary. Conventional devices, which provide for feeding therapeutically active substances to a humidified breathing gas stream, therefore often fall back on humidification by means of special devices, which is usually expensive and complicated. This may also be associated with the use of a large amount of consumable materials. Provisions may also be made, as an alternative, for eliminating humidifying altogether. However, this does, in turn, lead to the risk that the ciliary epithelium will dry out, which implies an increased risk for pneumonia. Finally, It is also possible to do away with an actually undesired longer duration of administration of therapeutically active substances. However, this does, in turn, imply a marked curtailment of the desired therapeutic possibilities.

SUMMARY OF THE INVENTION

Thus, the object of the present invention is to overcome these and other drawbacks of the state of the art. In addition, a cost-effective device, which can be manufactured with simple means, shall be created for providing a breathing gas stream.

In particular, a possibility shall be created for a therapeutic breathing gas stream, i.e., a gas stream, which contains a therapeutically active substance, to be able to be fed to a patient during flexible tube-based breathing assistance or respiration without the drawbacks of the state of the art.

Such a therapeutic breathing gas stream shall be able to be humidified in a physiologically adequate manner, and it shall guarantee at the same time a controlled and properly metered administration of the desired therapeutic substance. Administration shall be possible especially in the aerosol form.

To accomplish at least one of these objects, the present invention provides for a device for providing a breathing gas stream, which contains a therapeutically active substance, for the mechanical processing and/or mechanical breathing assistance of a patient, with features to avoid the mentioned drawbacks. A method for providing a breathing gas, which contains a therapeutically active substance, for the mechanical respiration and/or mechanical breathing assistance of a patient is also provided.

In such a device for providing a breathing gas stream, which contains a therapeutically active substance, for the mechanical respiration and/or mechanical breathing assistance of a patient, wherein the device has at least one line, through which a first gas stream flows during the operation of the device, and wherein the device has at least one second line, wherein the first line and the second line have a common flow section, and wherein the first line and the second line are separated from each other in the area of the common flow section by a water vapor-permeable membrane, the present invention provides for a second gas stream to flow through the second line during the operation of the device.

An exchange of substances can take place in the area of the common flow section between the first gas stream and the second gas stream in such a device. In particular, water vapor can diffuse through the water vapor-permeable membrane and thus be transferred from one gas stream into the other gas stream. It is conceivable with these features, for example, that one of the two gas streams contains the therapeutic substance to the administered (also called aerosol stream below) and the other of the two gas streams is a humidified air stream (gas stream). For example, water vapor can enter in this case the aerosol stream from the humidified air stream. The aerosol stream can likewise be humidified in this manner to a physiologically tolerable or even advantageous extent, without the therapeutic substance becoming lumped during the formation of the aerosol. The initial formation of the aerosol particles can rather take place in a more or less dry gas stream, so that a dry aerosol stream is formed at first. This means that the gas stream, which contains the therapeutically active substance (aerosol stream), is at first a dry gas stream. This dry gas stream can then likewise be humidified in the device according to the present invention by means of a humidified gas stream.

It is recognized that it is advantageous if the first or second gas stream contains the therapeutic substance to be administered, said substance preferably being an aerosol, especially preferably an aerosol capable of entering the alveoli. An aerosol capable of entering the alveoli is defined in this case as an aerosol whose aerosol particles have such a size that they can reach the alveoli of the lungs and be resorbed there.

It is recognized, furthermore, that it is favorable if the first or the second gas stream is a humidified gas stream.

In addition, it is favorable if the first line and the second line are arranged coaxially to one another in the area of the common flow section. The transfer of water vapor can take place especially uniformly due to the coaxial arrangement of the two lines in relation to one another. A coaxial arrangement or a coaxial flow is defined in the present invention such that the parts arranged coaxially in relation to one another have identical axes of rotation.

The device according to the present invention may have, furthermore, a breathing assistance device as well as a humidifying chamber. In addition, the device may have a device for admixing aerosol particles. This device for admixing aerosol particles may be, for example, an atomizer. However, other aerosol generators are conceivable as well. It is conceivable in this connection that one of the two lines, i.e., the first line or second line, is connected to the humidifying chamber, while the other of the two lines, i.e., the second line or first line, is connected to the device for admixing aerosol particles. The gas stream, which is flowing through the line that is connected to the breathing assistance device and the humidifying chamber, can be humidified in this manner. The gas stream that flows through the other line can be loaded, by contrast, with aerosol particles.

The gas stream that is loaded with aerosol particles may be generated in this connection by means of a separate pressurized gas source. The gas stream that is humidified may be generated by the breathing assistance device. For example, the first gas stream can be generated by means of the pressurized gas source and subsequently sent through the device for admixing aerosol particles, where it becomes the aerosol stream. The second gas stream can then be generated by the breathing assistance device and sent through the humidifying chamber of the device, where it becomes the humidified gas stream. The humidified gas stream and the aerosol stream can subsequently be sent through the common flow section, wherein the aerosol stream flows through the first line and wherein the humidified gas stream flows through the second line. The water vapor-permeable membrane may be formed in this case in the area of the common flow section such that it separates the first gas stream and the second gas stream from one another. An uncontrolled mixing of the humidified gas stream with the aerosol stream can be prevented in this manner and the first gas stream can be humidified in this manner in a controlled manner.

It is also favorable if the first line and/or the second line are of a flexible tube-like design. The first line and the second line are preferably of a flexible tube-like design in this case. For example, one of the two lines may be an inspiration tube or an expiration tube of the breathing assistance device.

It is advantageous, furthermore, in this connection if the first line and/or second line has a wall, preferably a flexible tube wall, which is formed in the area of the common flow section by a water vapor-permeable membrane. It is conceivable in this connection both that the membrane is formed in some sections only in the area of the common flow section and that the membrane extends over the entire area of the common flow section.

Provisions may, furthermore, be made for the first line to be arranged within the second line in the area of the common flow section. The first line may be, for example, a tube or a flexible tube, which consists, for example, of the above-described water vapor-permeable membrane. This flexible tube can be inserted, for example, into the flexible inspiration tube or into the flexible expiration tube of a device for mechanical respiration or for mechanical breathing assistance. The breathing gas stream, which is fed to the patient in connection with the mechanical respiration or mechanical breathing assistance, can thus flow, for example, around the first line during inspiration or expiration.

It is thus conceivable, for example, that the breathing gas stream, which may be, for example, the second gas stream, is provided by a breathing assistance device and is sent through a humidifying chamber before it enters the flexible inspiration tube. The flexible inspiration tube may represent the second line of the device in this case. The first line of the device can be plugged or inserted, as described above, into the flexible inspiration tube in this case. When the second gas stream, which was humidified by the humidifying chamber and is therefore a humidified gas stream, then flows into the flexible inspiration tube, it must flow around the first line. The second line may now be designed, for example, such that the second gas stream can flow spirally or helically around the first line in the area of the common flow section. An additional gas stream is sent to the patient within the first line in such an arrangement. This additional gas stream corresponds to the first gas stream and contains, as was described above, the therapeutic substance to be administered. Moisture can be transferred from the second gas stream into the first gas stream in such an arrangement by means of the membrane formed between the first line and the second line.

The quantity of moisture that passes over into the first gas stream and the velocity with which this happens can affect the properties of the aerosol that shall be fed into the patient's respiratory tract. It is especially important in this connection that the total quantity of moisture in the aerosol and the particle size of the aerosol particles are such that the aerosol is respirable, on the one hand, and that, on the other hand, the risk of deposits in the area of the upper airways or even of breathing out again are prevented from occurring to a great extent.

It is important, especially if the therapeutically active substance is a powder, to sufficiently humidify the atomized powder. Aerosol particles with such a mean mass aerodynamic diameter (MMAD) that they can enter the alveoli of the lungs, i.e., are respirable, should thus be formed. Such particles typically have an MMAD in the range of 0.5 m to 10 m, preferably 1 m to 5 m and especially preferably 1 m to 3 m.

It is especially advantageous in this connection if the first gas stream has a mean flow velocity of less than 3 m/sec, preferably 2.5 m/sec or less, especially preferably 2.2 m/sec or less, and especially preferably 2 m/sec or less. Such a flow velocity is sufficient to reliably transport the atomized aerosol particles from the atomizer to the patient.

It is preferred, furthermore, if the residence time of the first gas stream in the area of the common flow section is at least 1 sec or more, preferably at least 2 sec or more and especially preferably at least 3 sec or more.

It is also preferred if the residence time of the first gas stream in the area of the common flow section is at most 120 sec or less, preferably at most 90 sec or less and especially preferably at most 60 sec or less. Mist particles that can be optimally absorbed by the lungs can be optimally formed due to humidification of the atomized dry surfactant powder along the common flow section in case of such a residence time in the area of the common flow section and in case of a mean flow velocity as described above. The time during which the individual aerosol particles are present in the common flow section of the first and second lines of the device is sufficient for particles of the above-mentioned respirable size) to be formed.

It is especially advantageous in this case if the first gas stream is a laminar gas stream. Turbulence in the first gas stream is prevented from occurring in this case and the aerosol particles that are formed and develop are prevented from colliding with the wall of the first line and from possibly adhering there. Surfactant particles can thus likewise be prevented, for example, from growing in an uncontrolled manner during their transportation from the atomizer to the patient along the common flow section by colliding with one another and adhering to one another in the process.

Furthermore, it may be advantageous if the first line and/or second line has a heater. Especially the second line, which is arranged, for example, around the first line, can thus have a so-called flexible tube heater. This heats the stream to be humidified and facilitates the transfer of the water vapor into the first line. The first line may optionally have a flexible tube heater as well. This may be advantageous, for example, if the gas stream, which is sent through the first line, shall be fed to a patient without further mixing with the breathing gas stream provided. The gas stream thus provided can be preheated in this manner and can be taken up by the lungs in a physiologically adequate manner.

A temperature-measuring device may be provided, for example, for checking the temperature of the breathing gas stream. This temperature-measuring device may be arranged, for example, close to an adapter. Such an adapter may be used, for example, to establish a connection between the line system of the above-described device, i.e., between the first or second line of the device, and the airways of the patient to be treated. A mixing chamber, which makes it possible to bring together (mix) the therapeutic breathing gas stream provided through the first line with the moist breathing gas stream provided through the second line, may be present in the adapter. This controlled mixing would then take place immediately before the inhalation of the breathing gas stream by the patient.

The adapter may also be designed such that it is not or not only via aerosol particles contained in it that the first gas stream acts therapeutically, at least at times, but it brings about a reduction of the anatomic dead space in the manner of tracheal gas insufflation. No mixing of the gas streams takes place in the adapter in this case. The device according to the present invention may be a device for tracheal gas insufflation.

The device according to the present invention may be operated according to both the co-flow method and the counterflow method.

For example, the second gas stream may have, in the area of the common flow section, a principal direction of flow that corresponds to the direction in which the first gas stream flows as well (co-flow method). This may be the case, for example, when the first line is plugged or inserted into the flexible inspiration tube of a respirator. The flexible inspiration tube represents the second line of the device.

It is also conceivable that the second gas stream has, in the area of the common flow section, a principal direction of flow that is opposite the direction in which the first gas stream flows (counterflow method). This may be the case, for example, when the first line is inserted into the flexible expiration tube of a respirator. This is especially favorable if the patient to be treated shall be respirated by means of a two-tube method. However, respiration or breathing assistance of the patient is also possible, of course, by means of a single-tube method.

It is recognized that a device according to the present invention preferably has a breathing assistance device from which a flexible inspiration tube is led via a humidifying section to an adapter, which is in connection with the airways of a patient to be treated. The device according to the present invention may have, furthermore, a first line for a therapeutic gas stream, namely, the aerosol stream. This line may be branched off from the flexible inspiration tube. In addition, the line may optionally also be supplied with a gas stream from a pressurized gas supply unit. A control unit and a device for admixing aerosol particles are arranged between the pressurized gas supply unit and the first line. The gas stream, which arrives either from the first line connected to the flexible inspiration tube or from the additional pressurized gas supply unit, which is optionally present, is mixed with a therapeutic substance by means of this device for admixing aerosol particles, which is preferably an atomizer. This gas stream preferably represents the first gas stream according to the present invention and the line through which the gas stream flows corresponds to the first line according to the present invention. This line is preferably lead, at least in some sections, through the flexible inspiration tube or even through an optionally present flexible expiration tube of the device, so that the first line and the second line (namely, the flexible inspiration tube or flexible expiration tube) have a common flow section. This common flow section may also be called humidifying section. The flow of the first gas stream is guided in this area free from deflection to the extent possible, i.e., as a laminar gas stream, and with a mean flow velocity of preferably less than 2 m/sec. The first gas stream now forms an inner gas stream within the device, while the second gas stream represents an outer gas stream. The outer gas stream may flow coaxially to the inner gas stream along the humidifying section, i.e., along the common flow section. Coaxial arrangement or coaxial flow is defined in the present invention such that the parts arranged coaxially to one another have identical axes of rotation. A water vapor-permeable membrane, which separates the inner and outer gas streams from each other, is arranged between the inner gas stream and the outer gas stream. Moisture can pass over through this membrane from the outer gas stream into the inner gas stream as described above. It is recognized at any rate that the breathing gas streams, namely, the outer gas stream and the inner gas stream, enter the area of the common flow section with different moisture contents.

It may also be favorable, on the whole, if the main flow of the gas, i.e., of the first or second gas stream, preferably of the second, humidified gas stream, is led helically at least in one of the lines. For example, the outer, second gas stream may thus flow helically around the first line, through which the inner, first gas stream flows, in the area of the common flow section. For example, the second line may be formed for this with an inner surface that has the shape of a thread. It is also conceivable that the first line has an outer surface that has the shape of a thread. This outer surface of the first line forms an inner surface of the second line if the first line extends within the second line.

It is also advantageous if the device contains features that can be recognized by technical means that are contained in the device for admixing aerosol particles and which can be used to determine the compatibility. For example, the replaceable part of the device, e.g., the flexible inspiration tube or the flexible expiration tube, may be provided with means for identification by means of electromagnetic waves (radio frequency identification, RFID).

Furthermore, the present invention makes provisions in a method for providing a breathing gas stream, which contains a therapeutically active substance, for the mechanical respiration and/or mechanical breathing assistance of a patient, for the method to comprise the following steps:

a. Provision of a first gas stream
b. Feeding of the therapeutically active substance to the first gas stream
c. Provision of a second gas stream
d. Humidification of the second gas stream
e. Humidification of the first gas stream, which contains the therapeutically active substance, by means of the humidified second gas stream, wherein the humidification of the first gas stream in step e. is brought about by the humidified second gas stream and the first gas stream, which contains the therapeutically active substance, being sent simultaneously along a water vapor-permeable separating membrane, which separate the first gas stream and the second gas stream from each other.

The first gas stream can be humidified by means of such a method in an especially simple and turbulence-free manner, because if the first gas stream is flowing at a relatively low velocity along the first line of the device according to the present invention, moisture can be taken over from the side into the first gas stream along the entire line in the area of the separating membrane. However, this lateral transfer of the moisture takes place so uniformly that the inner, i.e., first gas stream is not swirled by this transfer. The first gas stream can thus flow as a laminar flow through the line.

The method may optionally also include as a further step:
f. the mixing of the humidified first gas stream with the humidified gas stream.

This may be advantageous, for example, if a partial area of the adapter or the entire adapter shall be filled with a gas mixture that shall supply a certain quantity of the therapeutically active substance, for example, surfactant.

It is recognized, on the whole, that it is advantageous in the sense of the present invention if a device according to the present invention is used to provide a breathing gas stream in a method as described above.

Further features, details and advantages of the present invention appear from the text of the claims as well as from the following description of exemplary embodiments on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
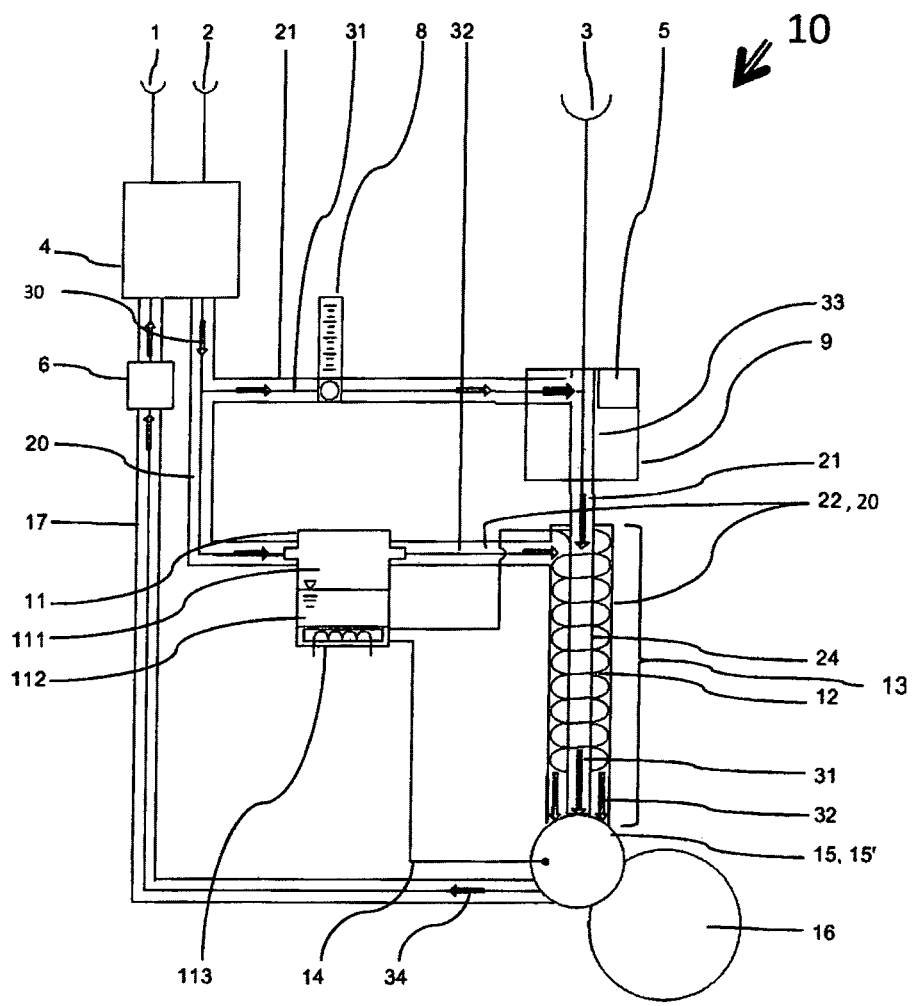
FIG. 1 is a schematic view of a device according to the present invention in a co-flow arrangement.

Referring to the drawings in particular, it is recognized in FIG. 1 that a patient 16 is connected to a device 10 according to the present invention via an adapter 15, 15'.

Device 10 has a breathing assistance device 4, a humidifying device 11, a control unit 5, a regulating device 8 as well as a device 9 for admixing aerosol particles.

The breathing assistance device 4 has a gas inlet 2 and a gas outlet 1. The breathing assistance device 4 is connected, in addition, to a flexible inspiration tube 20 and to an optionally present flexible expiration tube 17.

A first line 21, which leads to the regulating device 8, branches off from the flexible inspiration tube 20. The first line 21 leads from the regulating device 8 further to the device 9 for admixing aerosol particles. The first line 21 leads from the device 9 for admixing aerosol particles to the adapter 15.

The flexible inspiration tube 20 connects, in addition, the breathing assistance device 4 to the humidifying device 11. The humidifying device 11 comprises, just as the humidifying device 11 shown in FIG. 2, a heating device 113, a water reservoir 112 and a flow chamber 111. The flexible inspiration tube 20 leads as a second line 22 from the humidifying device 11 to the adapter 15. The second line 22 is thus part of the flexible inspiration tube 20.

It is recognized that the first line 21 and the second line 22 have a common flow section 13. This common flow section 13 is formed between the humidifying device 11 or the device 9 for admixing aerosol particles and the adapter 15. In other words, the common flow section 13 is formed downstream of the device 9 for admixing aerosol particles. The common flow section 13 is formed, in particular, in the area of the flexible inspiration tube 20. The first line 21 extends in the area of this common flow section 13 within the second line 22. The first line 21 and the second line 22 are arranged coaxially to one another, i.e., they have a common axis of rotation.

The breathing assistance device 4 is connected, furthermore, to the adapter 15 via the optionally present flexible expiration tube 17. The expired air 34 is sent back from the patient to the breathing assistance device 4 through the flexible expiration tube 17. Just like the expiration line 17 shown in FIG. 2, the expiration line 17 is provided with a filter 6.

It is recognized in FIG. 1 that the breathing assistance device 4 releases a breathing gas stream 30, which flows through the inspiration line 20. If a flexible expiration tube 17 is present, the expired air 34 flows back to the breathing assistance device 4 through the flexible expiration tube 17 in this example.

A first gas stream 31 is branched off from the breathing gas stream 30 in the area in which the first line 21 branches off from the inspiration line 20. The first gas stream 31 thus flows through the first line 21.

The first gas stream 31 is sent in this case from the first line 21 to the regulating device 8 and from there further to the device 9 for admixing aerosol particles.

FIG. 1 shows, furthermore, that a further, assisting gas stream 33 can be fed to the device 9 for admixing aerosol particles from an optionally present pressurized gas supply unit 3 via the control unit 5. Regardless of this feed of another gas stream 33, a therapeutically active substance is added to the first gas stream 31 in the device 9 for admixing aerosol particles 9. The device 9 for admixing aerosol particles 9 is preferably an atomizer. The first gas stream 31 is a therapeutic first gas stream 31, i.e., a gas stream 31, which contains a therapeutically active substance, after admixing the aerosol particles. This gas stream 31 is sent from the device 9 for admixing aerosol particles to the adapter 15, 15'. The first gas stream 31 is sent now along the common flow section 13.

The breathing gas stream, which remains after branching off the first gas stream 31 and flows further in the inspiration line 20 to the humidifying chamber 11, forms a second gas stream 32. This second gas stream 32 flows through the humidifying chamber 11 and can be humidified in the process. The second gas stream 32 enters from the humidifying chamber 11 the second line 22. Thus, the second gas stream 32, which arrives as a humidified gas stream from the humidifying chamber 11, consequently flows through the second line 22.

It is recognized in FIG. 1 that the humidified second gas stream 32 flows around the first line 21 extending within the second line 22 in the area of the common flow section 13. The humidified gas stream 32 of the second line 22 thus flows around the therapeutic breathing gas stream, i.e., the first gas stream 31, in the first line 21. A membrane 24 is arranged between the flow of the first line 21 and the second line 22 in the area of the common flow section 13. This membrane 24 separates the first gas stream 31 and the second gas stream 32 from each other. The membrane 24 forms, in this case, the wall (the full circumference of the tubular wall) of the first line 21 in the area of the common flow section 13. Membrane 24 is permeable to water vapor, so that moisture can pass over from the second gas stream 32 of the second line 22 into the therapeutic first gas stream 31 in the first line 21 in the area of the common flow section 13. The water vapor permeable membrane 24 may be, for example, Gore-Tex (PTFE or-Teflon®, respectively) or a pervaporation membrane, e.g., a membrane made of PBT (Polybutylenterephthalat) or the like.

It is recognized that the first gas stream 31 and the second gas stream 32 enter the common flow section 13 with different moisture contents. The moisture content of the first gas stream 31 will then become equalized with the moisture content of the second gas stream 32 over the course of the common flow section 13 due to moisture diffusing through the water vapor-permeable membrane 24. However, it is not necessary in the sense of the present invention at all for the two gas streams 31, 32 to reach an identical moisture content at the end. The first and second gas streams 31, 32 flow in the same direction as co-flows in the area of the common flow section 13. The device 10 is therefore in a co-flow arrangement.

Figure 2:
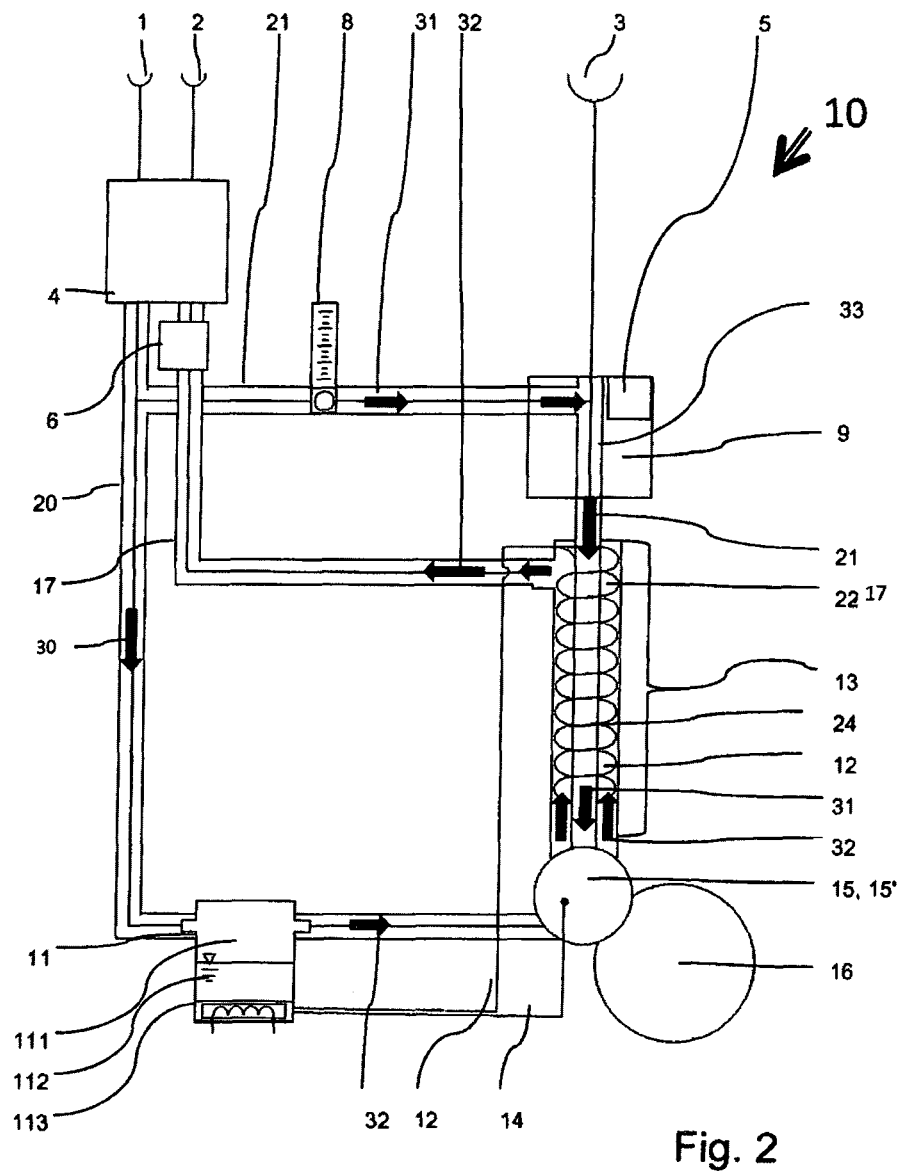
FIG. 2 is a schematic view of a device according to the present invention in the counterflow arrangement.

The device 10 according to the present invention in FIG. 1 has, furthermore, just like the device 10 shown in FIG. 2, a heater 12, which heats the second line 22. It is, for example, a resistance wire, a heating coil or a heating foil. Any other tube heater is likewise suitable in the sense of the present invention. The device shown in FIG. 1 has, furthermore, a temperature sensor 14 to check the temperature of the breathing gas stream. This preferably detects the temperature in the area of the adapter 15, 15'. It is possible in this manner to check, above all, whether the breathing gas stream flowing directly into the airways of the patient 16 has the desired physiological temperature.

A design according to the present invention of a device in a counterflow arrangement is recognized in FIG. 2. A patient 16 is connected to a device 10, according to the present invention, via an adapter 15 in this case as well. As was already described in reference to FIG. 1, adapter 15 is preferably a breathing mask. The device 10 has a breathing assistance device 4 with a gas inlet 2 and with a gas outlet 1, a humidifying device 11, a control unit 5, a regulating device 6 as well as a device 9 for admixing aerosol particles in this case as well.

The breathing assistance device 4 is connected to the humidifying device 11 via a flexible inspiration tube 20 in the example shown in FIG. 2 as well. The first line 21, which connects the breathing assistance device 4 to the regulating device 8 and leads from the regulating device 8 further to the device 9 for admixing aerosol particles, branches off from the flexible inspiration tube 20.

The flexible inspiration tube 20 leads in this example directly from the humidifying device 11 to the adapter 15. A flexible expiration tube 17 leads from the adapter 15 back to the breathing assistance device 4. The flexible expiration tube 17 represents the second line 22 in this exemplary embodiment. The first line 21 is arranged in this case in the area of the common flow section 13 in the flexible expiration tube 17. In other words, the second line 22 is part of the flexible expiration tube 17 in this case. The common flow section 13 is consequently also formed in the area of the flexible expiration tube 17, namely, between the adapter 15 and the device 9 for admixing aerosol particles or the breathing assistance device 4, in this exemplary embodiment.

It is thus recognized on the basis of FIGS. 1 and 2 that the common flow section 13 comprises in any case a section of the first line 21 that is formed between the device 9 for admixing aerosol particles and the adapter 15. In particular, the flow section 13 is formed downstream of the device 9 for admixing aerosol particles in reference to the first gas stream 31.

The first gas stream 31 is a gas stream that is branched off from the breathing gas stream 30 in the example shown in FIG. 2 as well. The second gas stream 32 is now the part of the breathing gas stream 30 that is humidified in the humidifying chamber 11. The second gas stream 32 is then inspired at first by the patient and flows as a humidified expiratory (expired) gas stream 32 through the expiration line 17, i.e., consequently through the second line 22. In the area of the common flow section 13, the principal direction of flow of the second gas stream 32 in the second line 22 is opposite the direction of flow of the first gas stream 31 in the first line 21. The first gas stream 31 and the second gas stream 32 are consequently led in a counterflow arrangement.

The present invention is not limited to one of the above-described embodiments, but may be varied in many different ways.

Adapter 15 is preferably a breathing mask. As an alternative, adapter 15 may also be an adapter 15' that is suitable for tracheal gas insufflation instead of a breathing mask.

Thus, the second line 22 may extend within the first line 21 in an alternative embodiment.

All the features and advantages appearing from the claims, the specification and the drawings, including design details, arrangements in space and method steps, may be essential for the present invention both in themselves and in a great variety of combinations.

It is recognized that it is advantageous in a device 10 for providing a breathing gas stream, which contains a therapeutically active substance, for the mechanical respiration and/or mechanical breathing assistance of a patient, wherein the device 10 has at least one first line 21, through which a first gas stream 31 flows during the operation of the device, wherein the first line 21 and the second line 22 have a common flow section 13, and wherein the first line 21 and the second line 22 are connected to one another by a water vapor-permeable membrane 24 (that forms the full circumference of the tubular wall) in the area of the common flow section 13, if a second gas stream 32 flows through the second line 22 during the operation of the device, wherein the first and second lines 21, 22 are arranged coaxially to one another in the area of the common flow section 13. It is favorable in this case, furthermore, if the first or second gas stream 31, 32 contains the therapeutic substance to be administered, wherein the substance is preferably an aerosol, especially preferably a respirable aerosol. It is advantageous, in addition, if the first or second gas stream 31, 32 is a humidified gas stream. It is favorable in this case if the first line 21 is arranged within the second line 22 in the area of the common flow section 13. It is advantageous, in particular, if the first line 21 and/or the second line 22 is designed as a flexible tube. Both lines 21, 22 are preferably in the form of a flexible tube in this case.

It is favorable in any case if the first line 21 and/or second line 22 has a wall, preferably a tube wall, which is formed by the water vapor-permeable membrane 24 in the area of the common flow section 13. It is advantageous in such a device if the first gas stream 31 has a mean velocity of flow of less than 3 m/sec, preferably 2.5 m/sec or less, especially preferably 2.2 m/sec or less, and especially preferably 2 m/sec or less during the operation of the device, if the residence time of the first gas stream 31 in the area of the common flow section 13 is at least 1 sec or more, preferably at least 2 sec or more and especially preferably at least 3 sec or more during the operation of the device, and/or if the residence time of the first gas stream 31 in the area of the common flow section 13 is at most 120 sec or less, preferably at most 90 sec or less and especially preferably at most 60 sec or less during the operation of the device. The first line 21 (the inner tube) may have a preferred diameter of 4 to 10 mm in case the device is used for neonates. The first line 21 (the inner tube) may have a preferred tube diameter of 8 to 25 mm in case the device is used for adults. The second line 22 (the outer tube) may have a tube diameter that is the size of the first line 21 and an additional 6 to 20 mm. The length of the common flow section 13 may be between 1 and 3 m in a preferred embodiment. It is possible for the length to vary between 0.5 and 3.5 m. The tube diameter of the inner tube 21 and the outer tube 22 is of course not restricted to the mentioned dimensions but can vary between 4 to 25 mm or even 3 to 30 mm. Also the outer diameter may be not only 6-20 mm larger than the inner diameter but may be larger in a range of 4-30-mm or about 3-25 mm larger than the Inner diameter.

It is recognized in this connection that it is favorable if the first gas stream 31 is a laminar gas stream. It may be advantageous now if the second gas stream 32 has a principal direction of flow that corresponds to the direction in which the first gas stream 31 is also flows in the area of the common flow section 13. However, it may also be advantageous if the second gas stream 32 has a principal direction of flow that is opposite the direction in which the first gas stream 31 flows in the area of the common flow section 13.

It is recognized, furthermore, that it is favorable in a method for providing a breathing gas stream that contains a therapeutically active substance for the mechanical respiration and/or mechanical breathing assistance of a patient if the method comprises the following steps:

a) Provision of a first gas stream 31, b) Feeding of the therapeutically active substance to the first gas stream 31, c) Provision of a second gas stream 32, d) Humidification of the first gas stream 31, which contains the therapeutically active substance, by means of the humidified second gas stream 32, wherein the humidification of the first gas stream 31 in step e) is carried out by the humidified second gas stream 32 and the first gas stream 31, which contains the therapeutically active substance, being sent simultaneously along a water vapor-permeable membrane 24, which separates the first gas stream 31 and the second gas stream 32 from one another.

It is especially advantageous if the method comprises as a further step f) the mixing of the humidified first gas stream 31 with the humidified second gas stream 32. The great advantage of the use of a device 10 according to the present invention for carrying out such a method is recognized in this connection.

While specific embodiments of the invention have been shown and described in detail to illustrate the application of the principles of the invention, it will be understood that the invention may be embodied otherwise without departing from such principles.

APPENDIX

LIST OF REFERENCE NUMBERS

| | |
|---|---|
| 1 | Gas outlet |
| 2 | Gas inlet |
| 3 | Pressurized gas supply unit |
| 4 | Breathing assistance device |
| 5 | Control unit |
| 6 | Filter |
| 8 | Regulating device |
| 9 | Device for admixing aerosol particles |
| 10 | Device |
| 11 | Humidifying device |
| 111 | Flow chamber |
| 112 | Water reservoir |
| 113 | Heating device |
| 12 | Heater |
| 13 | Common flow section |
| 14 | Temperature sensor |
| 15, 15' | Adapter |
| 16 | Patient |
| 17 | Flexible expiration tube |
| 21 | First line |
| 22 | Second line |
| 24 | Membrane |
| 30 | Breathing gas stream |
| 31 | First gas stream |

-continued

LIST OF REFERENCE NUMBERS

| | |
|---|---|
| 32 | Second gas stream |
| 33 | Gas stream |
| 34 | Expired air |

What is claimed is:

1. A device for providing a breathing gas stream, which contains a therapeutically active substance, for the mechanical respiration and/or mechanical breathing assistance of a patient, the device comprising:
a water vapor-permeable membrane;
a first line through which a first gas stream flows during the operation of the device, wherein a therapeutically active substance is delivered to the first gas stream;
a second line through which a second gas stream flows during the operation of the device, the second gas stream comprising a humidified gas stream, wherein the first line and the second line have a common flow section and the first line and the second line are connected to one another in the area of the common flow section by the water vapor-permeable membrane;
an adapter connected to, and being in flow connection with, the first line and the second line, the adapter establishing a flow connection between the first and second lines and an airway of the patient, the adapter including a mixing chamber to mix together the first and second gas streams.

2. The device in accordance with claim 1, wherein the first and second lines are arranged coaxially to one another in the area of the common flow section.

3. The device in accordance with claim 1, wherein the therapeutic substance is to be administered in the form of a respirable aerosol.

4. The device in accordance with claim 1, wherein the first line or the second line comprises a flexible tube.

5. The device in accordance with claim 1, wherein the first line and the second line have a common flexible tube wall, which is formed by the water vapor-permeable membrane in the area of the common flow section.

6. The device in accordance with claim 1, wherein the first line is arranged within the second line in the area of the common flow section.

7. The device in accordance with claim 1, wherein the residence time of the first gas stream, in the area of the common flow section, during the operation of the device is at least 1 sec.

8. The device in accordance with claim 1, wherein the first gas stream is a laminar gas stream.

9. The device in accordance with claim 1, wherein the second gas stream has a principal direction of flow that corresponds to the direction in which the first gas stream also flows, in the area of the common flow section.

10. A method for providing a breathing gas stream, which contains a therapeutically active substance, for the mechanical respiration and/or mechanical breathing assistance of a patient, the method comprising the steps of:
providing a device comprising a water vapor-permeable membrane, a first line through which a first gas stream flows during the operation of the device and a second line through which a second gas stream flows during the operation of the device, wherein the first line and the second line have a common flow section and the first line and the second line are connected to one another in the area of the common flow section by the water vapor-permeable membrane;

feeding of the therapeutically active substance to the first gas stream;

humidifying the second gas stream such that the second gas stream is a humidified second gas stream, said humidifying being performed before inhalation of the second gas stream by the patient; and humidifying the first gas stream, which contains the therapeutically active substance, by means of the humidified second gas stream, wherein the humidification of the first gas stream is carried out by the humidified second gas stream and the first gas stream, which contains the therapeutically active substance, being sent simultaneously along the water vapor-permeable membrane, which separates the first gas stream and the second gas stream from each other, the first gas stream comprising an average flow velocity of less than 3 m/s, wherein a residence time of the first gas stream in the common flow section is at least one second and at most 120 seconds, where the first and second gas streams are mixed prior to inhalation by the patient.

11. The method in accordance with claim 10, wherein:

the first gas stream contains the therapeutic substance to be administered in the form of a respirable aerosol.

12. The device in accordance with claim 1, wherein the first line has a diameter of eight to twenty-five millimeters, the second line comprising a second line diameter, the second line diameter being equal to at least the diameter of the first line, wherein a length of the common flow sections is equal to 0.5 m and 3.5 m.

13. A method for mechanically assisting breathing of a patient, the method comprising the steps of:

providing a breathing gas stream for mechanical inspiration of the patient;

dividing the breathing gas stream into a first gas stream and a separate second gas stream before inspiration by the patient;

adding a therapeutically active substance to the first gas stream after said dividing;

humidifying the second gas stream after said dividing, and before the inspiration of the second gas stream by the patient;

providing a common flow section with a first line and a second line, said first line and said second line in said common flow section each being defined, at least in part, by a water vapor-permeable membrane;

flowing the first gas stream through said first line of said common flow section after said step of adding the therapeutically active substance and before inspiration by the patient;

feeding the first and second gas streams to the patient for the mechanical inspiration of the patient, said step of feeding being performed after said step of adding the active substance, and after said step of humidifying the second gas stream.

* * * * *